US010695281B2

(12) United States Patent
Agerton et al.

(10) Patent No.: US 10,695,281 B2
(45) Date of Patent: Jun. 30, 2020

(54) LATE STAGE ADDITION OF RHEOLOGY MODIFIER

(71) Applicant: The Procter & Gamble Company, Cincinnati, OH (US)

(72) Inventors: Mark Lewis Agerton, Cincinnati, OH (US); Steven Robert Alexander, Colerain Township, OH (US); James Albert Berta, West Chester, OH (US); Gina Lynn Blum, Cincinnati, OH (US); Marco Caggioni, Cincinnati, OH (US); Susan Marie Dawes, Miami Township, OH (US); David Michael Farren, Mason, OH (US); Justin Thomas Lydon Hedin, Cincinnati, OH (US); Charles Phillip Miller, Cincinnati, OH (US); Christa Marie Novicki, Clay Township, OH (US); Melissa Cherie Payne, West Chester, OH (US); Molly Rose Schottelkotte, Sycamore Township, OH (US); John Christopher Wesner, Liberty Township, OH (US); Randall Lee Wood, Springboro, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 16/204,725

(22) Filed: Nov. 29, 2018

(65) Prior Publication Data

US 2019/0091126 A1    Mar. 28, 2019

Related U.S. Application Data

(63) Continuation of application No. 14/523,180, filed on Oct. 24, 2014, now Pat. No. 10,172,778.

(60) Provisional application No. 61/896,435, filed on Oct. 28, 2013, provisional application No. 61/897,348, filed on Oct. 30, 2013.

(51) Int. Cl.
| | |
|---|---|
| *A61K 8/73* | (2006.01) |
| *A61Q 11/00* | (2006.01) |
| *A61K 8/04* | (2006.01) |
| *A61K 8/02* | (2006.01) |
| *A61K 8/31* | (2006.01) |

(52) U.S. Cl.
CPC ............ *A61K 8/731* (2013.01); *A61K 8/0241* (2013.01); *A61K 8/042* (2013.01); *A61K 8/31* (2013.01); *A61K 8/73* (2013.01); *A61Q 11/00* (2013.01); *A61K 2800/80* (2013.01); *A61K 2800/805* (2013.01)

(58) Field of Classification Search
None
See application file for complete search history.

(56) References Cited

U.S. PATENT DOCUMENTS

| | | |
|---|---|---|
| 2,751,328 A | 6/1956 | Sanders |
| 2,946,725 A | 7/1960 | Norris et al. |
| 3,070,510 A | 12/1962 | Cooley et al. |
| 3,538,230 A | 11/1970 | Pader et al. |
| 3,862,307 A | 1/1975 | Di Giulio |
| 4,051,234 A | 9/1977 | Gieske et al. |
| 4,138,477 A | 2/1979 | Gaffar |
| 4,183,914 A | 1/1980 | Gaffar et al. |
| 4,340,583 A | 7/1982 | Wason |
| 4,420,312 A | 12/1983 | Wason |
| 4,421,527 A | 12/1983 | Wason |
| 4,599,363 A | 7/1986 | Miles et al. |
| 5,037,637 A | 8/1991 | Gaffar et al. |
| 5,176,899 A | 1/1993 | Montgomery |
| 5,236,696 A | 8/1993 | Catiis et al. |
| 5,320,832 A | 6/1994 | Catiis et al. |
| 5,827,505 A | 10/1998 | Hughes et al. |
| 5,939,052 A | 8/1999 | White, Jr. et al. |
| 6,149,894 A | 11/2000 | Yamane et al. |
| 6,213,166 B1 | 4/2001 | Thibiant et al. |
| 6,251,372 B1 | 6/2001 | Witt et al. |
| 6,692,726 B1 | 2/2004 | Morgan et al. |
| 7,220,404 B2 | 5/2007 | Morgan et al. |
| 9,795,552 B2 | 10/2017 | Tanner et al. |
| 2013/0025500 A1 | 1/2013 | Jones et al. |
| 2013/0230474 A1 | 9/2013 | Tanner |
| 2013/0243717 A1 | 9/2013 | Catalan et al. |
| 2013/0243834 A1 | 9/2013 | Tanner |
| 2013/0243835 A1 | 9/2013 | Tanner et al. |
| 2015/0352028 A1 | 2/2015 | Tanner et al. |
| 2015/0118168 A1 | 4/2015 | Agerton et al. |
| 2015/0118271 A1 | 4/2015 | Agerton et al. |
| 2018/0008525 A1 | 1/2018 | Tanner et al. |

FOREIGN PATENT DOCUMENTS

| | | |
|---|---|---|
| EP | 2551337 | 1/2013 |
| FR | 2246261 | 5/1975 |
| GB | 1544537 | 4/1979 |
| JP | S58208209 | 12/1983 |

OTHER PUBLICATIONS

Paul, Edward L., Atiemo-Obeng, Victor A., Kresta, Suzanne M. (2004). Handbook of Industrial Mixing—Science and Practice, John Wiley & Sons, pp. 358-360. Ait-Kadi, A., Marchal, P., Choplin, L., Chrissement, A., Bousmina.
Ait-Kadi, A., Marchal, P., Choplin, L., Chrissement, A., Bousmina, M., "Quantitative Analysis of Mixer-Type Rheometers using the Couette Analogy", Canadian J. Chem Eng., 80 (6), pp. 1166-1174, 2002.).
Hefferen, "Journal of Dental Research", Jul.-Aug. 1976, pp. 563-573.
International Search Report dated Jan. 27, 2015, 8 pages.

*Primary Examiner* — Susan T Tran
*Assistant Examiner* — William Craigo
(74) *Attorney, Agent, or Firm* — James E. Oehlenschlager; Jason J Camp

(57) ABSTRACT

Methods of making personal care compositions, such as dentifrices, involving the addition of rheology modifiers at a later stage in the personal care composition formation process.

19 Claims, 3 Drawing Sheets

LATE STAGE ADDITION OF RHEOLOGY MODIFIER

FIELD OF THE INVENTION

The present invention relates to methods of making personal care compositions, such as dentifrices, specifically methods involving the addition of rheology modifiers at a later stage in the personal care composition formation process.

BACKGROUND OF THE INVENTION

Dentifrice is typically made in vacuum vessels using some type of high energy mixing device, to combine the various components. The liquids are usually added to the vacuum vessel as a first step. Flavor or other oils can be added at various points within the batch during the mixing process to minimize loss and maximize within batch antifoaming benefits. The salts are added either directly to the mix tank or added to a slurry tank first then added to the mix tank. The abrasive is typically added directly to the mix tank, however it is possible the abrasive could be pre slurried and delivered to the mix tank as a premix.

Rheology modifiers are either added directly to the mix tank or added via offline pre slurry (tank or inline). The direct to the tank option requires significant within batch mixing (typically high energy) which can take significant processing time to complete. The offline option requires more capital assets to support the different formulations. Typically the final step of currently used processes is the addition of the surfactant. Keeping the surfactant to the end of the batch makes tank deaeration easier to complete. Even with holding the surfactant to the end of the process, when making the dentifrice batch on the residual of the previous batch, the residual surfactant from the first batch can cause significant challenges on deaeration. These challenges can account for up to 30% of the total process time in making toothpaste.

The ingredients are typically combined together in the mix tank by recirculating the ingredients through a high shear mixing device to create a final homogenous product composition. Vacuum is then applied to the mix tank to deaerate the dentifrice to the desired finished density. The addition of rheology modifiers thickens the premix making dearation more difficult, as it is harder to pull air out of a thick premix. Due to the addition of the rheology modifiers during the mixing process the premix has a paste like viscosity that clings to the internal mix tank surfaces, preventing the complete removal of the premix when it is pumped out of the mix tank. This requires the mix tank to be cleaned prior to making another product formula. It currently takes substantial length of time (>1 hr) and large amounts of water to clean a mix tank. This results in a greatly reduced making capacity due to lost time, as new formulas cannot be made while the system is being cleaned. Therefore due to the high viscosity of the finished product, processing time is slow and losses are high.

What is needed is a personal care composition making methodology that has reduced down-time due to inter batch cleaning times.

SUMMARY OF THE INVENTION

A method of producing a personal care composition is provided that comprises forming in a mix tank premix having a lower viscosity than a packaged personal care composition; transferring the premix from the mix tank; adding rheology modifier in line to the premix as the premix is transferred through the high energy dispersion device; deaerating the premix; and packaging the premix to produce a personal care composition.

A method of producing a personal care composition is provided that comprises forming in a mix tank premix having a lower viscosity than a packaged personal care composition; transferring the premix from the mix tank to a high energy dispersion device; adding rheology modifier in line to the premix as the premix is transferred through the high energy dispersion device; deaerating the premix using an inline deaeration device; and packaging the premix to produce a personal care composition; wherein the inline deaeration device is positioned such that the pressure drop between the high energy dispersion device and inline deaeration device is less than the pumping pressure head of the high energy dispersion device.

DETAILED DESCRIPTION OF THE INVENTION

Figure 1:
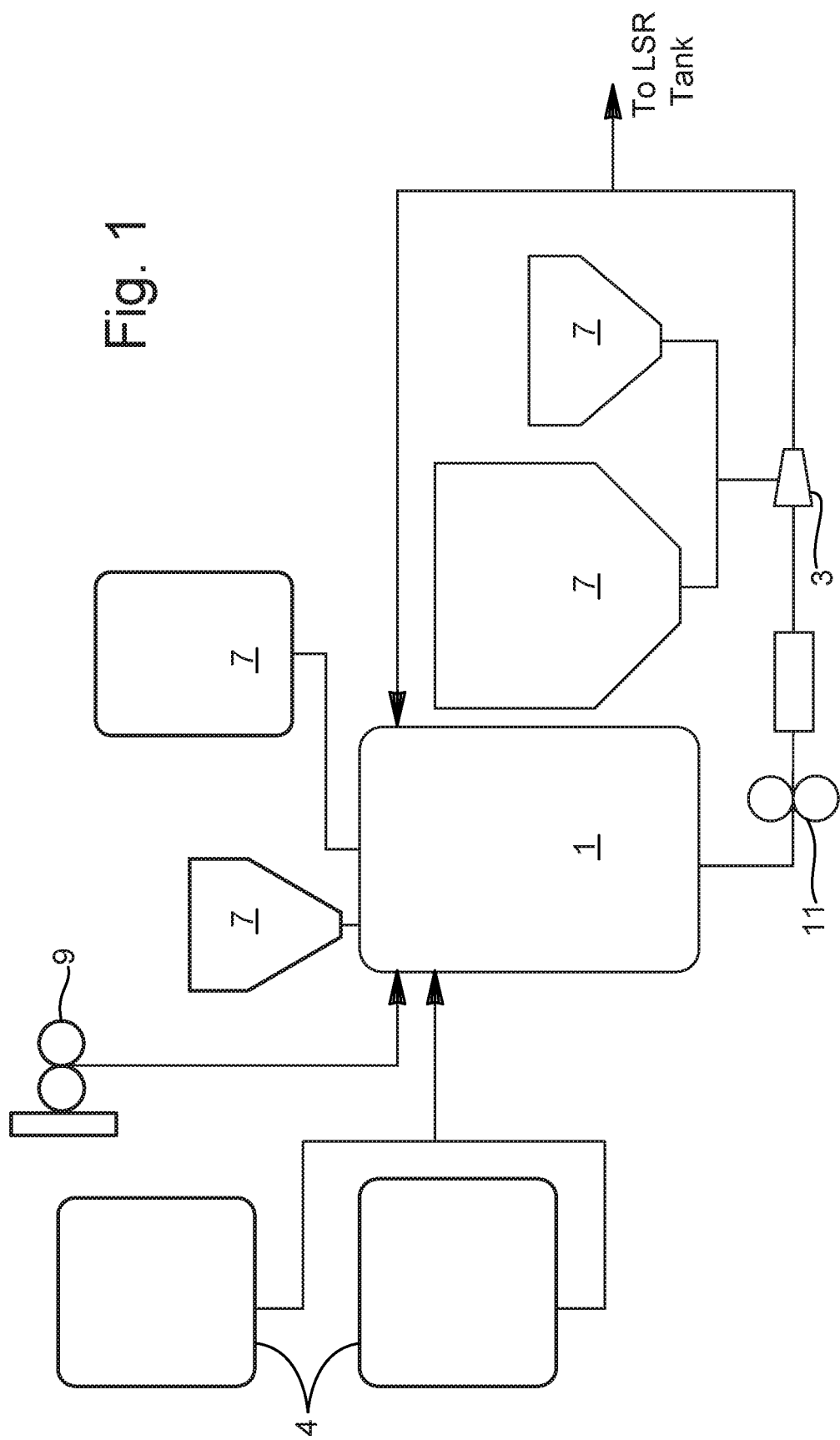
FIG. 1 is a process flow chart showing an embodiment of the present invention.

The present invention involves the late addition of rheology modifiers to a dentifrice premix. Losses from washout of the mix tank, due to a thickened premix, are minimized and throughput of the process in the mix tank is faster because of lower rheology. The low rheology of the premix also increases the efficiency and speed of deaeration, which may be conducted prior to an increase in viscosity, such as in line, prior to pumping through a high shear mill or in the mix tank. In certain embodiments the deaeration of the premix is done prior to the addition of surfactant to reduce the generation of micelles.

All parts, percentages and proportions referred to herein and in the claims are by weight of the total oral composition unless otherwise indicated. All measurements are made at 25 deg. C. on the total oral composition unless otherwise indicated.

As used herein, the word "or" when used as a connector of two or more elements is meant to include the elements individually and in combination; for example X or Y, means X or Y or both.

By "personal care composition" is meant a product which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, odor control or general aesthetics. Non-limiting examples of personal care compositions include hair coloring compositions, oral care compositions, after shave gels and creams, pre-shave preparations, shaving gels, creams, or foams, moisturizers and lotions, cough and cold compositions, leave-on skin lotions and creams, shampoos, conditioners, shower gels, bar soaps, toilet bars, antiperspirants, deodorants, depilatories, lipsticks, foundations, mascara, sunless tanners and sunscreen lotions.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

An illustrative processing diagram of the instant invention is depicted in FIG. 1. The mixing process begins with the addition of liquids 4 to the mix tank 1. The mix tank 1 provides the means for preparing a low viscosity slurry of the liquid and solid components of the mix. The liquids 4 can be added directly to the mix tank 1, or could be added through an high energy dispersion device, such as an eductor, examples of which include a Lobestar eductor sold by Vortex Ventures, Houston, Tex., allowing powders to be added concurrently with the liquids. After the main liquids (typically humectants, water, pH adjuster, and potentially flavor and emulsifier/surfactant) are added to the tank the powder (or remaining powder) 7 can be added to the mix tank 1. In certain embodiments the powder 7 can be added using an eductor 3, so as to maximize the dispersion during the addition, which minimizes the total processing time. The powders typically start with the salts for the system, then the addition of the abrasive(s). Visual ingredients, such as mica, prills, and aesthetic agents, can also be added at this point. After all the materials are combined, the batch is mixed for a time to deliver homogeneity (this time is a function of the type of dentifrice being made). Mixing can occur under vacuum, for example by using a vacuum pump 9, or under atmospheric conditions. In certain embodiments mixing under non-vacuum conditions can be done as the low viscosity of the fluid allows for self deaeration of the system. Being able to produce under non-vacuum conditions reduces the energy consumption of the system improving efficiency of the overall process. So when possible the batch is under atmospheric conditions in the mix tank at a temperature of about 15° C. to about 55° C. The lower viscosity enables shorter mix time to boost process efficiency.

For example, with reference to FIG. 1, in certain embodiments the mix tank 1 can be charged with Sorbitol, Water, Pigment, Dye and Polysorbate 80 through the main port and the agitator controller set to provide sufficient tank turnovers to maintain homogeneity. To determine sufficient mixing, a relationship between the system pumping rate and the settling rate of the suspension can be used to calculate the system suspension ratio. A system suspension ratio of about one or greater insures a system will not settle and maintain homogeneity. The system suspension ratio can be determined by first measuring the settling rate of the suspension. Once the settling rate of the suspension is determined, the pumping rate of the system can be calculated. The system suspension ratio is calculated as follows:

$$\frac{Qp}{SRf \times Vb} = SSR$$

where: Qp—system pumping rate (see following discussion) (m3/s)
Vb—Equivalent batch volume (m3)
SRf—settling rate of the fluid measured by attached method (l/s)
SSR—System Suspension Ratio Qp can be measured using a flow meter on an external recirculation loop or by the following calculation approach for calculating the pumping rate of the agitator in a stirred tank; as shown in: Paul, Edward L. Atiemo-Obeng, Victor A. Kresta, Suzanne M. (2004). Handbook of Industrial Mixing—Science and Practice. John Wiley & Sons. p. 358-360.

$$Q = N_Q \times N \times D^3$$

Where
$N_Q$=Pumping number which depends on the impeller type, D/τ ratio and impeller Reynolds number
and the impeller Reynold's number is:

$$Re = \frac{\rho \times N \times D^2}{\mu}$$

N=impeller speed
D=Diameter of the impeller

The Table below gives values for the pumping number for various impellers under turbulent conditions. In certain embodiments the pumping number is between about 0.4 $N_Q$ to 0.8 $N_Q$.

TABLE 1

| Impeller Type | $N_Q$ |
|---|---|
| Propeller | 0.4-0.6 |
| Pitched blade turbine | 0.79 |
| Hydrofoil impellers | 0.55-0.73 |
| Retreat curve blade | 0.3 |
| Flat-blade turbine | 0.7 |
| Disk flat-blade turbine (Rushton) | 0.72 |
| Hollow-blade turbine (Smith) | 0.76 |

Figure 2:
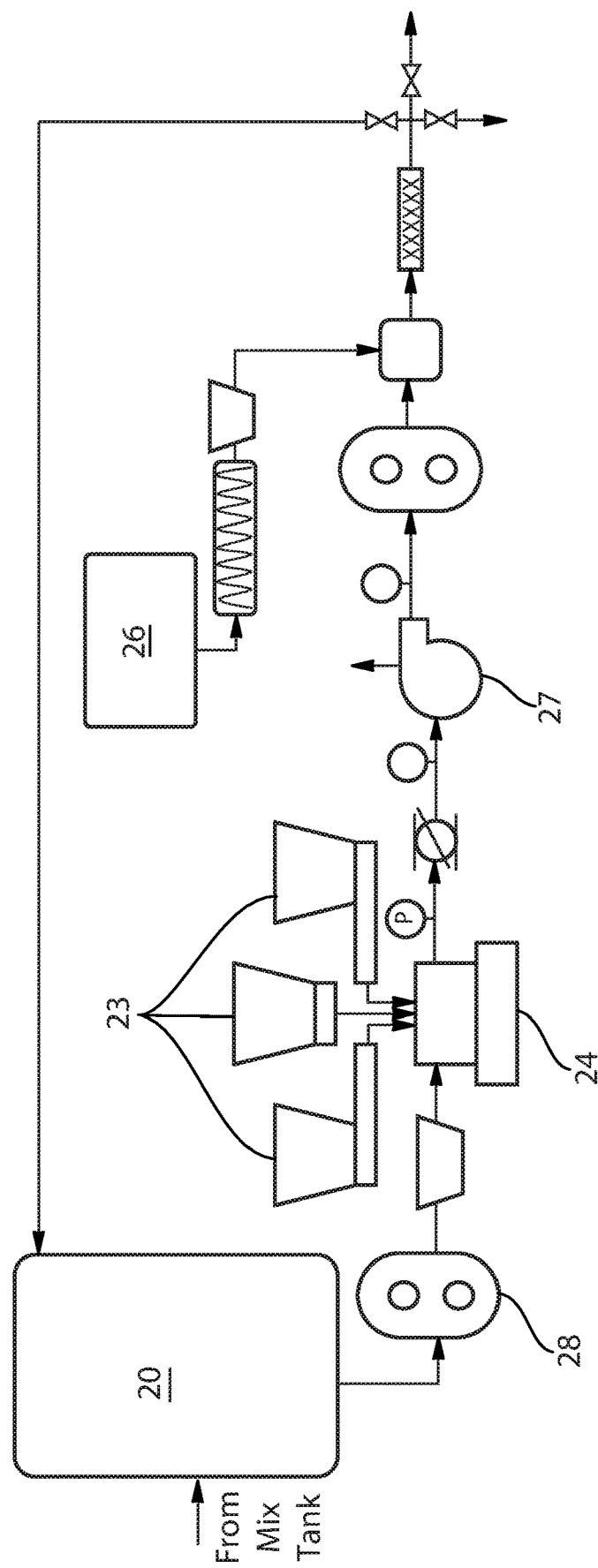
FIG. 2 is a process flow chart showing an embodiment of the present invention.

The calculated system suspension ratio is a ratio of pumping rate/settling rate and in certain embodiments can be greater than 0.75 or greater than 1. In certain embodiments as shown in FIG. 1, for producing premix a recirculation pump 11 controller can be set to provide a system suspension ratio of about two or greater and is typically between about 30-Hz to about 60 Hz and the mixture can be recirculated through the eductor 3 for about 5 minutes or less. A flavor component can then be added to the mix tank 1 through a main port while mixing and recirculating through the eductor 3. A powder delivery hose can be connected to the eductor 3 via a powder delivery port and the Minor powders (sweetener, fluoride source, phosphates, etc.) can then be added to the mix tank 1 through the eductor 3 via the powder delivery hose connected to the powder delivery port. The batch is recirculated through the eductor 3 for about 5 minutes or less, or until pass volume of 100% of batch volume has been achieved. Sodium hydroxide can then be added to the mix tank 1 via the main port and the batch recirculated through eductor 3 for about 5 minutes or less. Silica can then be added to the mix tank 1 through the eductor 3 via the powder delivery hose connected to powder delivery port and the batch again recirculated through the eductor 3 for about 5 minutes or less, or until pass volume of 100% of batch volume has been achieved. The recirculation through the eductor 3 can then be turned off while continuing to mix via agitation at a system suspension rate of about 1.5 or greater, until the batch is transferred into a Late Stage Rheology (LSR) feed tank 20 or fed directly into the LSR system, as shown in FIG. 2. Vacuum can then be applied on the mix tank 1 to remove residual batch material from lines and transfer to LSR tank 20. It is possible to coat the mix chamber of the premix tank to reduce premix adhesion to the surface of the mix chamber, for example with a substance like poly(tetrafluoroethene), which could further reduce the losses within the tank.

In certain embodiments, it is possible to add a small amount of rheology modifier to the premix while it is in the mix tank, as an aspect of the present invention involves low viscosity, such that when the premix viscosity is measured at 0.1/s after letting the sample rest for 30-60 minutes, the viscosity should be below 150 Pa·s to minimize the residual in the system and maintain the improved system efficiency.

The agitator controller on the LSR tank 20 can be set to maintain the system suspension ratio of about one or greater. In certain embodiments a dust collection system can be turned on to minimize dust in the production area. Sufficient quantities (by weight) of rheology modifiers and additives are confirmed and available for use in the feeder hoppers 23 and the feeder hoppers are placed within an high energy dispersion device 24, such as a Quadro ZC1 24 (Quadro Engineering, Ontario, Canada). After confirming that a Surfactant tank 26 contains a sufficient quantity of material, the desired personal care composition recipe, such as a dentifrice recipe is selected, for example from a LSR Human Machine Interface (HMI), and setpoints are matched with the Formula Card and batch production record (BPR). The high energy dispersion device 24 speed can be set between about 40 Hz and about 60 Hz, with the Process Control valve (PCV) 25 setpoint between about 10% and about 90% open and inline deaeration device 27, such as a Yokota pump ASP-515 or ASP-610 (Yokota Manufacturing Co. Ltd., Hiroshima, Japan), which may have a speed setpoint between about 45 Hz and about 60 Hz. The relatively small internal volume, and pumping efficiency of the Yokota ASP-515 or ASP-610 pump, provides an advantage versus traditional inline deaeration devices.

The above LSR system can be started in recirculation mode. The typical temperature of the premix within the process can be between about 10° C. and 60° C., as in certain embodiments a higher temperature than about 60° C. runs the risk of negatively impacting the flavor display of the system. Further, in certain embodiments a temperature lower than about 10° C. becomes energy prohibitive for keeping/getting the fluid to that low temperature. The feed flow rate of the LSR Feed Pump 28 can be confirmed at setpoints between about 40 L/min and about 250 L/min). The rheology modifier feeder hoppers 23 are monitored while dispensing at the target rates as defined by the formula card to produce a desired personal care composition.

Viscosities of the premix may range from about 0.01 Pa·s to about 10 Pa·s when sampled at 10 sec-t. In certain embodiments the viscosity may be measured with an AR2000 rheometer (TA Instruments, New Castle, Del.). The AR2000 rheometer uses the following methodology when measuring rheology: For the conditioning step, the temperature is set to 25 C and equilibration is performed for 2 minutes. Steady state flow with increasing shear rate is measured by ramping the shear rate (l/s) from 0.001 to 120.0 and setting to Log mode. Three (3) points per decade are acquired at 25° C. over a sampling period of 3.0 seconds within a tolerance of 5% until two (2) consecutive points within the tolerance are achieved. The maximum point is measured over a time of 1.0 minute. Steady state flow with decreasing shear rate is measured by ramping the shear rate (l/s) from 120.0 to 0.01 and setting to Log mode. Three points per decade are acquired at 25° C. over a sampling period of 10.0 seconds within a tolerance of 5% until two consecutive points within the tolerance are achieved. The maximum point is measured over a time of 1.0 minute.

Once the premix is sufficiently mixed as defined by the system suspension ratio, as stated previously, it is then transferred out of the LSR tank 20 through a pump and flow meter into a high energy dispersion device 24 (i.e. rotor stator mill), such as a Quadro ZC1, in certain embodiments at a flow rate from about 10 Kg/min to about 1000 Kg/min or from about 40 Kg/min to about 400 Kg/min. The high energy dispersion device ensures an even dispersion of the rheology modifiers within the main mix stream. In certain embodiments the rheology modifiers are added to the high energy dispersion device at a controlled rate so that they comprise between about 0.01% to about 4% individually or between about 0.1% to about 10% collectively, by weight of the personal care composition, to ensure the right formula ratios are delivered. The rheology modifiers can be added in the form of dry powder, agglomerated powder, agglomerated powder with other ingredients, premixed powder with other dry ingredients, or premixed powder with liquid ingredients. A coating, for example mineral oil, can be added to a rheology modifier further impacting how the rheology modifier disperses or hydrates in the system.

One embodiment of this system would be loss in weight feeders feeding individual rheology modifiers into the high energy dispersion device. Typically, soon after adding the rheology modifiers, the premix rheology begins to increase. The rate of viscosity increase is a function of the type of rheology modifier used, the formulation, and process conditions. It is also possible to add visual solid ingredients via the high energy dispersion device as well. This approach can provide further process efficiency benefits by reducing the number of times the premix needs to be changed over, and allowing efficient splitting of premixes into different finished product lots. Examples of rheology modifiers that can be added via this approach are: xanthan gum, carboxymethyl cellulose, carrageenan, carbomer, hydroxyethyl cellulose, guar gum, or thickening silica. Examples of visual solid ingredients are titanium dioxide, polyethyelene specs, prills, pigmented silicas, or mica.

After leaving the high energy dispersion device the premix then may flow through an inline deaeration device 27, such as a Yokota pump ASP-515 or ASP-610. The inline deaeration device can remove down to about 0.001% by volume of the premix or less air, as measured by sonar detection method, which is below the consumer noticeable air level of about 0.5% by volume or greater air, enabling a robust process window. In certain embodiments the inline deaeration device can reduce the air level of the premix to about 0.01% or less, by volume of the premix. In still further embodiments the inline deaeration device may deliver the ratio of air removal to liquid throughput of about 0.15 L/Kg to about 0.6 L/Kg or from about 0.2 L/Kg to about 0.5 L/Kg. In addition the size of the inline deaeration device may deliver a loss (waste in deaerater)/throughput ratio of about 1 l/s to about 8 l/s or from about 2 l/s to about 4 l/s. The inline deaeration may occur after all dry ingredients have been added to the stream, so that the air removal can be maximized Given that the rheology modifiers begin increasing rheology as soon as they are added to the premix (as defined by the rate of hydration of the system). The rate of hydration of the formulations is a function of numerous formula components such as rheology modifier type, water level, ionic strength, solids loading and other attributes. In addition, the rate of hydration is driven by process conditions such as temperature and energy density of the high energy dispersion device.

It is also important that the deaeration occur at a rheology lower than finished product, such as toothpaste to maximize efficiency (rate), as less energy is required to remove air from a material having a lower rheology as compared to a material having a higher rheology. Consequently the inline deaeration device may be located as close to the high energy dispersion device as possible. The inline deaeration device can be positioned such that the pressure drop between the high energy dispersion device and inline deaeration device is less than the pumping pressure head of the high energy dispersion device. In certain embodiments if that is not possible then the pressure control valve can be replaced with a positive displacement pump to control back pressure on the high energy dispersion device and ensure the premix can be fed to the inline deaeration device. This relationship may be defined by the residence time of the rheology modifiers from the point of premix contact through the inline deaeration device and the rate of hydration of the system.

Deaeration efficiency can be improved by reducing or removing foaming surfactants, such as sodium lauryl sulfate. Therefore, in certain embodiments the dentifrice foaming surfactants are added after the deaeration steps. Emulsifying surfactants such as polysorbate 80 can be used prior to the deaeration step without appreciable impact to the deaeration efficiency.

The viscosity of the stream between the high energy dispersion device, and inline deaeration device in certain embodiments is between about 0.01 Pa·s and about 1,000 Pa·s measured at 10 sec−1 and in certain other embodiments between about 0.01 Pa·s and about 100 Pa·s measured at 10 sec−1 using the measurement protocol described above.

The energy density, or the amount of energy transferred to the premix by a piece of equipment, of the high energy dispersion device is best defined by the observed mechanical energy of the device (typically measured off the VFD or servo motor) and the premix flow rate through the system. This energy density has been shown to impact the personal care composition texture and the overall rate of hydration of the system. Acceptable energy density as described above would be between about 0.5 KW/Kg/s to about 11 KW/Kg/s or from about 3 KW/Kg/s to about 9 KW/Kg/s. It has also been observed that the energy to achieve acceptable texture is inversely related to the rate of hydration when other process conditions are held constant, such as temperature. The relationship of rate of hydration to minimal energy density is typically in the range of about 0.001 Kg/KWs² to about 0.10 Kg/KWs². The values are calculated by the following equation:

$$\frac{(\mu 10 \text{ s} - \mu 0)}{(\mu 0)(10 \text{ s})} \bigg/ \frac{PD}{Q} = RHpmED$$

where: µ10 s—viscosity measured 10 seconds after dispersed thickener added (Pa·s)
µ0—viscosity measured of system prior to addition of water soluble polymer (Pa·s)
PD—Power Draw (KW)
Q—system flow rate (Kg/s)
RHpmED—Rate of Hydration per minimal Energy Density [rate of hydration in relation to the energy density of the system versus the rate of hydration by itself]; (Kg/KWs²)

The following is a description of the method for determining the rate of hydration. With the development of a test mixing vessel and mix impeller, it is possible to understand the evolving rheology while combining multiple fluid streams, liquids and powders, or combinations of materials utilizing a conventional rotational rheometer that correlates to larger scale manufacturing processes. The conventional rotational rheometer offers the benefits of a precisely controlled motor and a highly sensitive torque sensor. Liquid/liquid and liquid/powder combinations can be created utilizing a test mixing vessel and impeller system. The test mixing vessel and impeller are designed to aid in dispersion of powders and/or liquids into other fluids.

Equipment

Test mixing vessel dimensions are optimized to impeller design to provide adequate liquid/liquid or liquid/solid mixing. For the rate of hydration experiments, a typical experimental design is detailed below for one impeller type and was the design used to support the rate of hydration data included in this application. For other impellers, test mixing vessel internal diameter and height, as well as impeller diameter, gaps, etc., will be optimized for that impeller.

Figure 3:
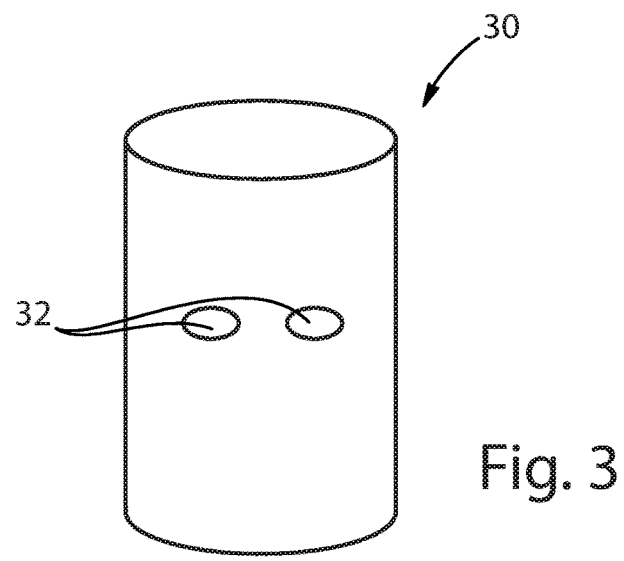
FIG. 3 is a perspective view of a test mixing vessel.
Figure 4:
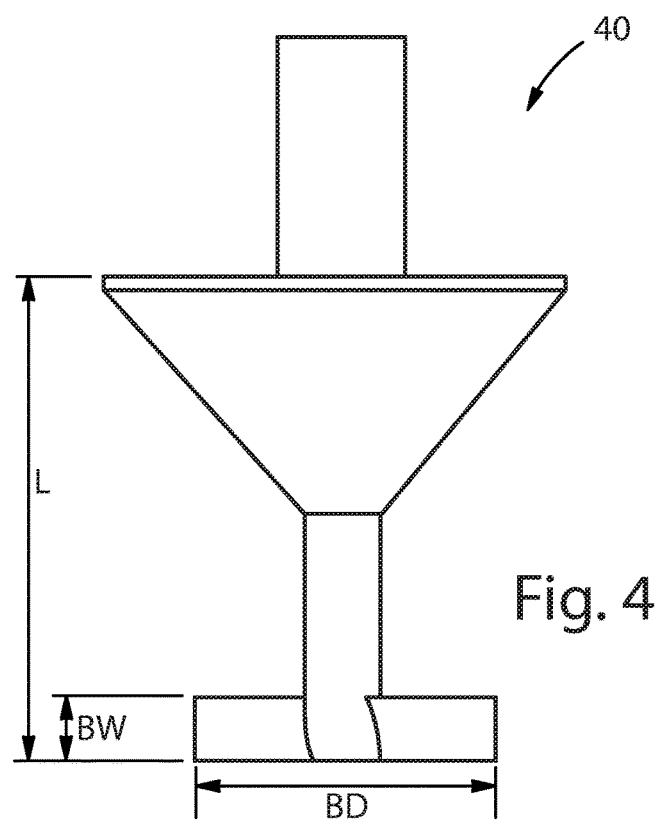
FIG. 4 is a side view of a mix impeller.

1. Test mixing vessel:
   a. The test mixing vessel is designed to be a miniature version of a traditional mix tank Test mixing vessel is constructed of plastic material, typically optically clear acrylic or polyvinyl chloride (PVC). As shown in FIG. 3 the test mixing vessel 30 is cylindrical in shape with a flat bottom and two separate injection ports 32 for material addition.
   b. Test mixing vessel dimensions:
      i. Internal diameter: 38.3 mm
      ii. Outside diameter: 42 mm
      iii. Vessel height: 65 mm
      iv. Injection port diameter: 5 mm, round, spaced 30 mm apart approximately 35 mm from vessel bottom
2. Mix impeller:
   a. As shown in FIG. 4, mix impeller 40 is an impeller design that combines a traditional pitch blade turbine with a hydrofoil impeller design. Dimensions for the mix impeller corresponding to above test mixing vessel are as follows:
      i. Mix impeller blade diameter (BD): 32.5 mm
      ii. Mix impeller blade width (BW): 13 mm
      iii. Length of mix impeller shaft (L): 55 mm
3. Rheometer:
   a. TA Instruments ARG2 or DHR3 controlled stress rheometer (TA Instruments, New Castle, Del.) equipped with custom peltier base container holder.
4. Methodology:
   a. Determine density of dentifrice base fluid via density meter, pygnometer, etc.

b. Based on fluid density, weigh appropriate amount of dentifrice base material to provide 28-30 mL of fluid into test mixing vessel.

c. Prepare polymer/binder slurries and pre-weigh appropriate combinations to meet the product formula card for dosing
   i. The binder slurries can be prepared in a system that allows the polymer to be dispersed without significant swelling. For example, 40% xanthan gum dispersed in PEG 300, 5% carbopol dispersed in acidified water, etc.

d. Mount test mixing vessel onto base holder and align/center mix impeller with test mixing vessel e. Lower mix impeller into mix chamber of test mixing vessel. Typical side wall gap between mix impeller and test mixing vessel is around 5.5 mm Gap will vary for alternative impeller types and test mixing vessel dimensions.

f. Rheometer methodology
   i. A traditional flow-peak hold experiment design is utilized where viscosity and torque are monitored as a function of shear rate over time.
   ii. Rheometer is set to desired temperature
   iii. Mix impeller speed is set at desired rpm to generate desired shear rate of the impellers. Desired shear rate typically ranges from 1 to several hundred $s^{-1}$.
   iv. Length of experiment may vary from 1 minute to 10 minutes depending on the formulation being created. Some formulations with lower water need to be analyzed over longer time periods up to 1 hour.
   v. Time, torque, and viscosity data is collected over the course of the experiment at the rate of 0.5 to 1 seconds per data point.

g. With impeller in place, start analysis program as powder and/or binder slurry is injected into test mixing vessel through the side ports in less than two seconds.

h. Monitor viscosity and torque over the measurement time with a sampling rate of less than once per second.

i. After the defined test run is complete (typically a 10 minute run), perform Metzner-Otto corrections to raw data (Ait-kadi A., Marchal P., Choplin L., Chrissement, A., Bousmina M., "Quantitative Analysis of Mixer-Type Rheometers using the Couette Analogy", Canadian J. Chem Eng., 80 (6), 1166-1174, 2002.).

After leaving the inline deaeration device the premix can then flow to a liquid injection system where the remaining premix surfactants can be added to complete the formula. It can be desirable to minimize the residence time between the high energy dispersion device and the liquid injection system so as to minimize the pressure drop across the system Minimizing the pressure drop across the system allows for smaller more efficient equipment and smaller line diameters. The smaller equipment is typically lower cost to purchase and operate; and the smaller lines typically have less loss. In certain embodiments the average residence time between the high energy dispersion device and the liquid injection system is from about 5 s to about 30 s. The rate of hydration and throughput are related via the following equation:

$$\frac{(\mu 30\ s - \mu 0)}{(\mu 0)(30\ s)} \Big/ Q = RHpT$$

where: $\mu 30\ s$—viscosity measured 30 seconds after rheology modifier added (Pa·s)
$\mu 0$—viscosity measured of system prior to addition of rheology modifier (Pa·s)
Q—system flow rate (Kg/s)
RHpT—Rate of Hydration per Throughput [relationship of rate of hydration over system throughput]; $(Kg/s^3)$ It has been observed that values of RHpT below 0.001 $Kg/s^3$ and up to 1 Kg/s3 provide acceptable pressure drop through a static mixing system. It is possible that values above 1 $Kg/s^3$ could be supported with dynamic mixing options as discussed below.

In certain embodiments the surfactants are incorporated within the stream by in line mixing technology, such as through using static mixers. In certain embodiments most of the surfactant is added after the inline deaeration device so as to maximize efficiencies of the inline deaeration process. Static mixers are well known in the art and are generally in the form of a series of repeating or random, interlocking plates and, or fins. Static mixers that can be used in the present invention include the Chemineer SSC.75-4R-S (KMA 4 element ¾") available from Chemineer Inc., Dayton, Ohio 45401 and the Koch SMX 4 element mixer (¾" nominal) available from Koch-Glitsch LP Mass Transfer Sales and Engineering, Cincinnati, Ohio Another type of mixer is that may be used is a dynamic mixer. One type of dynamic mixer is a high shear mill, such as those available from IKA Works, Wilmington, N.C. Further, if desired, static mixers or other inline mixers may be disposed in or with one or more of the inlet tubes or upstream of the confluence region. Additionally, surge tanks may be used to provide more constant flow for materials combined by the process described and claimed herein. Additionally or alternatively a Zanker plate may be utilized.

The choice of mixer can be influenced by the phase structure of the resultant composition and optimizing the pressure drop across the system, which is influenced by the rate of hydration. For example, for mixing some materials which are used to produce an isotropic composition, a static mixer is sufficient. For mixing other materials to produce a lamellar composition, greater agitation can be used to build the viscosity of the resultant composition. Therefore, a dynamic mixing system may be appropriate, such as a high shear mill. A dynamic mixing system as used herein is inclusive of the batch and continuous stir systems which use an impeller, jet mixing nozzle, a recirculating loop, gas percolation, rotating or fixed screen or similar means of agitation to combine materials therein.

A finished personal care composition, such as toothpaste, in certain embodiments, may have a viscosity ranging from about 1 Pa·s to about 200 Pa·s or from about 1 Pa·s to about 150 Pa·s measured at 1 sec−1. In certain embodiments the viscosity can be measured on an AR2000 rheometer (TA Instruments, New Castle, Del.). The AR2000 rheometer uses the following methodology when measuring rheology: For the conditioning step, the temperature is set to 25 C and equilibration is performed for 10 minutes. Steady state flow with increasing shear rate is measured by ramping the shear rate (1/s) from 0.001 to 120.0 and setting to Log mode. Three (3) points per decade are acquired at 25° C. over a sampling period of 3.0 seconds within a tolerance of 5% until two (2) consecutive points within the tolerance are achieved. The maximum point is measured over a time of 1.0 minute. Steady state flow with decreasing shear rate is measured by ramping the shear rate (1/s) from 120.0 to 0.01 and setting to Log mode. Three points per decade are acquired at 25° C. over a sampling period of 10.0 seconds within a tolerance of 5% until two consecutive points within the tolerance are achieved. The maximum point is measured over a time of 1.0 minute. After leaving this step the premix can be packaged, for example, into one or more containers having equal or unequal volumes. The container(s) containing the product may be ultimately shipped and sold to the consumer, or may be used for transport and storage of the mixture as an intermediate. Thus, the container(s) may be selected from a bulk storage device, for example, a tank, a tank car, or rail car, or a final package, for example, a tube, bottle and/or a tottle. Storing in the interim containers for a given amount of time could improve filling performance for striping. The container(s) may be provided with a frangible or resealable closure as are well known in the art, and be made of any material suitable for containing the materials combined according to the present invention.

In certain embodiments, one or more of the processing methods described herein may be employed or in conjunction with one or more additional processing methods and the products produced by employing multiple processing methods may be discharged into a common container, thereby forming for example, a product having multiple layers, phases, patterns etc. Such layers, phases and/or patterns may or may not mix in the container to form a homogeneous product. In certain embodiments, the processing method to manufacture a first phase of a product may be in a separate location from the processing method to produce a second or multiple phases for filling the container with the final multi-phase composition, such as a dentifrice with a paste phase and a gel phase.

In one aspect, the processing method or multiple methods can be a coupled with a filling line to fill containers with a first phase, a second phase, combined phase and/or a multiphase composition. In one aspect, where the composition is intended to be combined with another composition to form a multiphase product it may be filled into containers in many ways. For example, one could fill containers by combining toothpaste-tube filling technology with a spinning stage design.

Additionally, the present invention can be filled into containers by the method and apparatus as disclosed in U.S. Pat. No. 6,213,166. The method and apparatus allows two or more compositions to be filled in a spiral configuration into a single container using at least two nozzles to fill a container, which is placed on a rotating stage and spun as the composition is introduced into the container.

Examples of some of the components that can be used to make dentifrice according to the methods of the present invention are listed below.

As the sweetener, saccharin sodium, sucrose, maltose, lactose, stevioside, neohesperidildigydrochalcone, glycyrrhizin, perillartine, p-methoxycinnamic aldehyde and the like may be used in an amount of 0.05 to 5% by weight of the toothpaste. Essential oils such as spearmint oil, peppermint oil, salvia oil, eucalptus oil, lemon oil, lime oil, wintergreen oil and cinnamon oil, other spices and fruit flavors as well as isolated and synthetic flavoring materials such as 1-menthol, carvone, anethole, eugenol and the like can be used as flavors. The flavor may be blended in an amount of 0.1 to 5% by weight of the toothpaste. Ethyl paraoxy benzonate, butyl paraoxy benzoate, etc. may be used as the preservative. The sweetner may be added with the abrasive. The flavor and the preservative may be added when preparing the liquid of the slightly swollen rheology modifier or mixed with rheology modifier after mixing with the humectant. Enzymes such as dextranase, lytic enzyme, lysozyme, amylase and antiplasmin agents such as EPSI-LON-aminocaproic acid and tranexamic acid, fluorine compounds such as sodium monofluorophosphate sodium fluoride and stannous fluoride, chlorhexidine salts, quaternary ammonium salts, aluminum chlorohydroxyl allantoin, glycyrrhetinic acid, chlorophyll, sodium chloride and phosphoric compounds may be used as the effective ingredient. Moreover, silica gel, aluminum silica gel, organic acids and their salts may be blended as desired. An organic effective ingredient with low viscosity may be added when preparing the liquid of the slightly swollen rheology modifier.

The mix should have sufficiently low viscosity while being mixed in the mix tank, while having sufficiently high viscosity at the end of the dentifrice formulation process to prevent the product flowing off the brush once dispensed. Therefore a rheology modifier should provide the mix with minimal viscosity increase while in the mix, but increase the viscosity between the time the mix exits the mix tank and the dentifrice is loaded into a dispensing container.

Typically, rheology modifiers imparting the highest level of pseudoplasticity are those which form structure by charge-charge interactions or hydrogen-bonding such as the colloidal silicas and hectorite clays. From a flow rate standpoint, these materials have ideal characteristics, being highly shear thinning Rheology modifiers forming cross-linked networks, such as polysaccharide derivatives including xanthan gum or synthetic polymers including carbomer, also give a high degree of pseudoplasticity. Rheology modifiers that build structure by chain entanglement alone, such as cellulose gum, are also pseudoplastic, but tend to have a lower level of pseudoplasticity than those having a three dimensional order.

Rheology modifiers may be used singly, or in combination to form "thickening systems". Some rheology modifiers, such as hectorite, allow phase separation of the compositions in which they are used in the absence of a second rheology modifier. Similarly, there may be restrictions on the level at which an individual rheology modifier can be employed, requiring the addition of a further rheology modifiers to achieve the required rheology profile.

For a particular rheology modifier or combination of rheology modifiers, achieving the correct rheological profile to allow the premix to have a suitable flow rate during mixing yet form a useable dentifrice will be dependent upon the formulation level at which the rheology modifier or combination of rheology modifiers is employed. Typically, increasing the level of rheology modifier will lead to an increase in viscosity. Therefore, there is a window of rheology modifier levels that allows the mix to mostly exit the mix tank and to produce dentifrice that will be retained on the bristles. The optimal level or levels of rheology modifier or a combination of rheology modifiers will also be determined by the grade of material employed, typically as a function of molecular weight or polymer chain length, with longer chain lengths resulting in higher viscosity. The rheology modifier may also exhibit synergistic interaction with other ingredients in the formulation such that the level required to attain the correct viscosities during mixing and dentifrice use is altered. Many other factors may govern the selection of a particular rheology modifier in a particular formulation. A specific charge on the rheology modifier may be required for example in order to avoid undesirable interactions with other ingredients.

Rheology modifiers suitable for use in the present invention include organic and inorganic rheology modifiers, and mixtures thereof. Inorganic rheology modifiers include hectorite and derivatives, hydrated silicas, ternary and quaternary magnesium silicate derivatives, bentonite and mixtures thereof. Preferred inorganic rheology modifiers are hectorite and derivatives, hydrated silicas and mixtures thereof. Organic rheology modifiers include xanthan gum, carrageenan and derivatives, gellan gum, hydroxypropyl methyl cellulose, sclerotium gum and derivatives, pullulan, rhamsan gum, welan gum, konjac, curdlan, carbomer, algin, alginic acid, alginates and derivatives, hydroxyethyl cellulose and derivatives, hydroxypropyl cellulose and derivatives, starch phosphate derivatives, guar gum and derivatives, starch and derivatives, co-polymers of maleic acid anhydride with alkenes and derivatives, cellulose gum and derivatives, ethylene glycol/propylene glycol co-polymers, poloxamers and derivatives, polyacrylates and derivatives, methyl cellulose and derivatives, ethyl cellulose and derivatives, agar and derivatives, gum arabic and derivatives, pectin and derivatives, chitosan and derivatives, resinous polyethylene glycols such as PEG-XM where X is >=1, karaya gum, locust bean gum, natto gum, co-polymers of vinyl pyrollidone with alkenes, tragacanth gum, polyacrylamides, chitin derivatives, gelatin, betaglucan, dextrin, dextran, cyclodextrin, methacrylates, microcrystalline cellulose, polyquaterniums, furcellaren gum, ghatti gum, psyllium gum, quince gum, tamarind gum, larch gum, tara gum, and mixtures thereof. Preferred are xanthan gum, carrageenan and derivatives, gellan gum, hydroxypropyl methyl cellulose, sclerotium gum and derivatives, pullulan, rhamsan gum, welan gum, konjac, curdlan, carbomer, algin, alginic acid, alginates and derivatives, hydroxyethyl cellulose and derivatives, hydroxypropyl cellulose and derivatives, starch phosphate derivatives, guar gum and derivatives, starch and derivatives, co-polymers of maleic acid anhydride with alkenes and derivatives, cellulose gum and derivatives, ethylene glycol/propylene glycol co-polymers, poloxamers and derivatives and mixtures thereof. More preferred are xanthan gum, carrageenan and derivatives, gellan gum, hydroxypropyl methyl cellulose, sclerotium gum and derivatives, pullulan, rhamsan gum, welan gum, konjac, curdlan, and mixtures thereof.

Amounts of rheology modifiers may range from greater than 0.5% up to 4%, greater than 0.5% up to 3%, or greater than 0.5% up to 2% by weight of the total composition.

The toothpastes produced by the methods of the present invention may comprise greater than about 0.1% by weight of a surfactant or mixture of surfactants. Surfactant levels cited herein are on a 100% active basis, even though common raw materials such as sodium lauryl sulphate may be supplied as aqueous solutions of lower activity. Suitable surfactant levels are from about 0.1% to about 15%, from about 0.25% to about 10%, or from about 0.5% to about 5% by weight of the total composition. Suitable surfactants for use herein include anionic, amphoteric, non-ionic, zwitterionic and cationic surfactants, though anionic, amphoteric, non-ionic and zwitterionic surfactants (and mixtures thereof) are preferred.

Useful anionic surfactants herein include the water-soluble salts of alkyl sulphates and alkyl ether sulphates having from 10 to 18 carbon atoms in the alkyl radical and the water-soluble salts of sulphonated monoglycerides of fatty acids having from 10 to 18 carbon atoms. Sodium lauryl sulphate and sodium coconut monoglyceride sulphonates are examples of anionic surfactants of this type. In certain embodiments, a toothpaste comprises at least about 0.125%, at least about 0.5% anionic surfactant, or at least about 2%.

Suitable cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; benzalkonium chloride; cetyl trimethylammonium bromide; di-isobutylphenoxyethyl-dimethylbenzylammonium chloride; coconut alkyltrimethyl-ammonium nitrite; cetyl pyridinium fluoride; etc. Certain cationic surfactants can also act as germicides in the compositions disclosed herein.

Suitable nonionic surfactants that can be used in the compositions of the present invention can be broadly defined as compounds produced by the condensation of alkylene oxide groups (hydrophilic in nature) with an organic hydrophobic compound which may be aliphatic and/or aromatic in nature. Examples of suitable nonionic surfactants include the poloxamers; sorbitan derivatives, such as sorbitan di-isostearate; ethylene oxide condensates of hydrogenated castor oil, such as PEG-30 hydrogenated castor oil; ethylene oxide condensates of aliphatic alcohols or alkyl phenols; products derived from the condensation of ethylene oxide with the reaction product of propylene oxide and ethylene diamine; long chain tertiary amine oxides; long chain tertiary phosphine oxides; long chain dialkyl sulphoxides and mixtures of such materials. These materials are useful for stabilising foams without contributing to excess viscosity build for the oral composition.

Zwitterionic surfactants can be broadly described as derivatives of aliphatic quaternary ammonium, phosphonium, and sulphonium compounds, in which the aliphatic radicals can be straight chain or branched, and wherein one of the aliphatic substituents contains from about 8 to 18 carbon atoms and one contains an anionic water-solubilising group, e.g., carboxy, sulphonate, sulphate, phosphate or phosphonate.

The dentifrices produced by the methods of the present invention may comprise greater than about 50% liquid carrier materials. Water is usually present. Water employed in the preparation of commercially suitable dentifrice may be deionised and free of organic impurities. Water generally comprises at least 10%, preferably from about 20% to 70% by weight of the liquid dentifrice compositions herein. More preferably the compositions include at least about 30% water, suitably from about 30% to about 50% water. These amounts of water include the free water which is added plus that which is introduced with other materials such as with sorbitol and with surfactant solutions.

Generally the liquid carrier will further include one or more humectants. Suitable humectants include glycerin, sorbitol, and other edible polyhydric alcohols, such as low molecular weight polyethylene glycols at levels of from about 15% to about 50%. To provide the best balance of foaming properties and resistance to drying out, the ratio of total water to total humectant is preferably from about 0.65:1 to 1.5:1, preferably from about 0.85:1 to 1.3:1.

The viscosities of the oral compositions herein may be affected by the viscosity of Newtonian liquids present in the composition. These may be either pure liquids such as glycerin or water, or a solution of a solute in a solvent such as a sorbitol solution in water. The level of contribution of the Newtonian liquid to the viscosity of the non-Newtonian oral composition will depend upon the level at which the Newtonian liquid is incorporated. Water is typically present in a significant amount in an oral composition, and has a Newtonian viscosity of approximately 1 mPa·s at 25 deg. C. Humectants such as glycerin and sorbitol solutions typically have a significantly higher Newtonian viscosity than water. As a result, the total level of humectant, the ratio of water to humectant, and the choice of humectants, is critical to determining the high shear rate viscosity of the oral compositions.

Common humectants such as sorbitol, glycerin, polyethyleneglycols, propylene glycols and mixtures thereof may be used, but the specific levels and ratios used will differ depending on the choice of humectant. Sorbitol may be used, but due to its relatively high Newtonian viscosity, typically cannot be incorporated at levels above 45% by weight of the composition, as it contributes significantly to the high shear rate viscosity of the oral composition. Conversely, propylene glycol may be employed at higher levels as it has a lower Newtonian viscosity than sorbitol, and hence does not contribute as much to the high shear rate viscosity of the oral composition. Glycerin has an intermediate Newtonian viscosity in between that of sorbitol and polyethylene glycol.

Ethanol may also be present in the oral compositions. These amounts may range from 0.5 to 5%, optimally from 1.5 to 3.5% by weight of the total composition. Ethanol can be a useful solvent and can also serve to enhance the impact of a flavour, though in this latter respect only low levels are usually employed. Non-ethanolic solvents such as propylene glycol may also be employed. Also useful herein are low molecular weight polyethylene glycols.

The oral composition herein will typically comprise a variety of other components such as abrasives, fluoride ion sources, chelating agents, antimicrobials, rheology modifiers, silicone oils and other adjuvants such as preservatives and coloring agents.

The dentifrices produced by the methods of the present invention may comprise a dental abrasive. Abrasives serve to polish the teeth, remove surface deposits, or both. The abrasive material contemplated for use herein can be any material which does not excessively abrade dentine. Suitable abrasives include insoluble phosphate polishing agents, such as, for example, dicalcium phosphate, tricalcium phosphate, calcium pyrophosphate, beta-phase calcium pyrophosphate, dicalcium phosphate dihydrate, anhydrous calcium phosphate, insoluble sodium metaphosphate, and the like. Also suitable are chalk-type abrasives such as calcium and magnesium carbonates, silicas including xerogels, hydrogels, aerogels and precipitates, alumina and hydrates thereof such as alpha alumina trihydrate, aluminosilicates such as calcined aluminium silicate and aluminium silicate, magnesium and zirconium silicates such as magnesium trisilicate and thermosetting polymerised resins such as particulate condensation products of urea and formaldehyde, polymethylmethacrylate, powdered polyethylene and others such as disclosed in U.S. Pat. No. 3,070,510. Mixtures of abrasives can also be used. The abrasive polishing materials generally have an average particle size of from about 0.1 to about 30 preferably from about 1 to 15

The oral compositions described herein may have Radioactive Dentin Abrasion ("RDA") values of from about 70 to about 200, from about 70 to about 140, or from about 80 to about 125. The RDA values are determined according to the method set forth by Hefferen, "Journal of Dental Research", July-August 1976, pp. 563-573, and described in the Wason U.S. Pat. Nos. 4,340,583, 4,420,312 and 4,421,527.

Non-abrasive materials, such as polyphosphates can also contribute to a RDA value. A RDA value can, however, be measured for an abrasive in the absence of these materials. In the compositions of the present invention it is preferred that the abrasives themselves have a RDA value of from about 70 to about 140 or from about 80 to about 125 when used at a 5% loading.

Silica dental abrasives of various types offer exceptional dental cleaning and polishing performance without unduly abrading tooth enamel or dentin. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, for example silica xerogels marketed under the tradename "Syloid" by W. R. Grace & Company, Davison Chemical Division. Suitable precipitated silicas include those marketed by INEOS under the trade names Sorbosil AC 43 and AC 33. Silicas may be used that have an oil absorption from 30 g per 100 g to 100 g per 100 g of silica. It has been found that silicas with low oil absorption levels are less structuring, and therefore do not build the viscosity of the oral composition to the same degree as those silicas that are more highly structuring, and therefore have higher oil absorption levels. As used herein, oil absorption is measured by measuring the maximum amount of linseed oil the silica can absorb at 25 deg. C.

Suitable abrasive levels may be from about 0% to about 20% by weight of the total composition, in certain embodiments less than 10%, such as from 1% to 10%. In certain embodiments abrasive levels from 3% to 5% by weight of the total composition can be used.

For anticaries protection, a source of fluoride ion will normally be present in the oral composition. Fluoride sources include sodium fluoride, potassium fluoride, calcium fluoride, stannous fluoride, stannous monofluorophosphate and sodium monofluoro-phosphate. Suitable levels provide from 25 to 2500 ppm of available fluoride ion by weight of the liquid dentifrice.

Another optional agent is a chelating agent, of value as an anticalculus agent. Suitable chelating agents include organic acids and their salts, such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is possible to use a chelating agent which has an affinity for calcium that is too high, resulting in tooth demineralisation. In certain embodiments the chelating agents have a calcium binding constant of about 101 to 105 to provide improved cleaning with reduced plaque and calculus formation. The amounts of chelating that may be used in the formulations of the present invention are about 0.1% to about 2.5%, from about 0.5% to about 2.5% or from about 1.0% to about 2.5%. The tartaric acid salt chelating agent can be used alone or in combination with other optional chelating agents.

Another group of agents particularly suitable for use as chelating agents in the present invention are the water soluble polyphosphates, polyphosphonates, and pyro-phosphates which are useful as anticalculus agents. The pyrophosphate salts used in the present compositions can be any of the alkali metal pyrophosphate salts. An effective amount of pyrophosphate salt useful in the present composition is generally enough to provide at least 1.0% pyrophosphate ion or from about 1.5% to about 6% of such ions. The pyrophosphate salts are described in more detail in Kirk & Othmer, Encyclopedia of Chemical Technology, Second Edition, Volume 15, Interscience Publishers (1968).

Water soluble polyphosphates such as sodium tripolyphosphate, potassium tripolyphosphate and sodium hexametaphosphate may be used. Other long chain anticalculus agents of this type are described in WO98/22079. Also preferred are the water soluble diphosphonates. Suitable soluble diphosphonates include ethane-1-hydroxy-1,1-diphosphonate (EHDP) and aza-cycloheptane-diphosphonate (AHP). The tripolyphosphates and diphosphonates are particularly effective as they provide both anti-tartar activity and stain removal activity without building viscosity as much as much as less water soluble chemical stain removal agents and are stable with respect to hydrolysis in water. The soluble polyphosphates and diphosphonates are beneficial as destaining actives. Without wishing to be bound by theory, it is believed that these ingredients remove stain by desorbing stained pellicle from the enamel surface of the tooth. Suitable levels of water soluble polyphosphates and diphosphonates are from about 0.1% to about 10%, from about 1% to about 5%, or from about 1.5% to about 3% by weight of the oral composition.

Still another possible group of chelating agents suitable for use in the present invention are the anionic polymeric polycarboxylates. Such materials are well known in the art, being employed in the form of their free acids or partially or preferably fully neutralised water-soluble alkali metal (e.g. potassium and preferably sodium) or ammonium salts. Additional polymeric polycarboxylates are disclosed in U.S. Pat. Nos. 4,138,477 and 4,183,914, and include copolymers of maleic anhydride with styrene, isobutylene or ethyl vinyl ether, polyacrylic, polyitaconic and polymaleic acids, and sulphoacrylic oligomers of MW as low as 1,000 available as Uniroyal ND-2.

Also useful for the present invention are antimicrobial agents. A wide variety of antimicrobial agents can be used, including stannous salts such as stannous pyrophosphate and stannous gluconate; zinc salt, such as zinc lactate and zinc citrate; copper salts, such as copper bisglycinate; quaternary ammonium salts, such as cetyl pyridinium chloride and tetradecylethyl pyridinium chloride; bis-biguanide salts; and nonionic antimicrobial agents such as triclosan. Certain flavour oils, such as thymol, may also have antimicrobial activity. Such agents are disclosed in U.S. Pat. Nos. 2,946,725 and 4,051,234. Also useful is sodium chlorite, described in WO 99/43290.

Antimicrobial agents, if present, are typically included at levels of from about 0.01% to about 10%. Levels of stannous and cationic antimicrobial agents can be kept to less than 5% or less than 1% to avoid staining problems.

In certain embodiments antimicrobial agents are non-cationic antimicrobial agent, such as those described in U.S. Pat. No. 5,037,637. A particularly effective antimicrobial agent is 2',4,4'-trichloro-2-hydroxy-diphenyl ether (triclosan).

An optional ingredient in the present compositions is a silicone oil. Silicone oils can be useful as plaque barriers, as disclosed in WO 96/19191. Suitable classes of silicone oils include, but are not limited to, dimethicones, dimethiconols, dimethicone copolyols and aminoalkylsilicones. Silicone oils are generally present in a level of from about 0.1% to about 15%, from about 0.5% to about 5%, or from about 0.5% to about 3% by weight.

Sweetening agents such as sodium saccharin, sodium cyclamate, Acesulfame K, aspartame, sucrose and the like may be included at levels from about 0.1 to 5% by weight. Other additives may also be incorporated including flavours, preservatives, opacifiers and colorants. Typical colorants are D&C Yellow No. 10, FD&C Blue No. 1, FD&C Red No. 40, D&C Red No. 33 and combinations thereof. Levels of the colorant may range from 0.0001 to 0.1%.

EXAMPLE

To determine rate of viscosity generation using late stage rheology modifier addition, several toothpaste formulations were prepared, see TABLE 2 below.

TABLE 2

| Premix Components | High Sorbitol Sample (weight in grams) | High Water Sample (weight in grams) | Low Water Sample (weight in grams) |
| --- | --- | --- | --- |
| Sodium Fluoride | 0.093 | 0.101 | 0.104 |
| Glycerin | | | 13.754 |
| Propylene Glycol | | | 4.039 |
| Polyethylene Glycol 600 | | | 0.852 |
| Sorbitol | 29.791 | 10.145 | 2.046 |
| Water | 0.840 | 16.177 | 2.100 |
| Silica | 6.633 | 6.222 | 10.011 |
| Tetra Sodium Pyrophosphate | | | 2.369 |
| Sodium Phosphate | 0.588 | | |
| Sodium Pyrophosphate | | 1.323 | |
| Sodium Hydroxide | | 0.705 | 0.741 |
| Sodium Bicarbonate | | | 3.834 |
| Peppermint oil | 0.402 | 0.415 | 0.447 |
| Saccharin Sodium | 0.111 | 0.166 | 0.173 |
| FD&C Yellow No.. 5 | 0.044 | | |
| FD&C Blue 1 | 0.022 | | 0.426 |
| Titanium Dioxide | | 0.104 | |
| Poloxamer 407 | | | 0.170 |
| Polysorbate 80 | 0.004 | 0.004 | |
| Premix Addition Totals | 38.529 | 35.362 | 41.066 |
| Late Addition Premix 1 Components | | | |
| Polyethylene Glycol 300 | 0.829 | 1.504 | 1.500 |
| Xanthan Gum | | 0.104 | 0.400 |
| Carboxymethylcellulose Sodium | 0.332 | 0.498 | 0.200 |
| Late Addition Premix 2 Components | | | |
| Water | 1.946 | 2.489 | |
| Carbopol | 0.097 | 0.124 | |
| Totals | 40.904 | 38.576 | 41.666 |

Each of the Samples (High Sorbitol Sample, High Water Sample, Low Water Sample) were prepared using the late rheology modifier addition of the present invention and the rate of hydration measured according to the methodology detailed below, and previously described. Rate of Hydration was measured as a way to describe the viscosity of the system in relation to the short process times. Measuring product viscosity is common practice for fluids processing. Late addition of the rheology modifier makes the relative time impact of viscosity critical to understand and it demands that understanding occur on timescales historically ignored in batch processing.

Equipment:

The Test mixing vessel used to prepare the Sample premixes had an internal diameter of 38.3 mm, outside diameter of 42 mm, vessel height of 65 mm, and two injection ports that had a diameter of 5 mm, were spaced 30 mm apart, and positioned 35 mm from the vessel bottom. The Mix impeller used to mix the premix in the Test mixing vessel had a blade diameter of 32.5 mm, blade width of 13 mm, and the length of the Mix impeller shaft was 55 mm. The rheometer was a TA Instruments ARG2 controlled stress rheometer (TA Instruments, New Castle, Del.) equipped with custom peltier base container holder.

Methodology:

For each Sample the Premix components were added to the Test mixing vessel in the amounts shown in TABLE 2. The Late Addition Premix 1 and 2 components were mixed in an offline container until visually mixed and free of lumps for later addition to the premix. The Test mixing vessel was mounted unto a base holder and the Mix impeller aligned within the Test mixing vessel and lowered into the Test mixing vessel chamber with a gap of 5.5 mm. The Rheometer was set to 25° C. The rheometer test parameter was set for a flow peak curve with a shear rate set point of 25 sec−1 and data was collected over 10 minutes with 1 data point per second. With the Mix impeller in place, the TA Rheology Advantage program (TA Instruments, New Castle, Del.) was started and at the 5 second point injected, using a 5 ml or 10 ml syringe, the late addition premix 1 and 2 in less than three seconds via the two injection ports. Using the rheometer, viscosity, shear stress, shear rate, and temperature were measured. The shear rate was adjusted to 64 sec−1 using the rheometer and Metzner Otto relationship. The viscosity data from prior to the injection of Late Addition Premix 1 and 2 was used at the v0, the viscosity data from 10 seconds after the Late Addition Premix 1 and 2 were added was used as v10 s, and the viscosity data from 30 seconds after the Late Addition Premix 1 and 2 were added was used as v30 s and so on. The Rate of Hydration for each Sample was determined using the following equations:

$$\frac{(\mu 10 \text{ s} - \mu 0)}{(\mu 0)(10 \text{ s})} = RH_{10 \text{ s}}$$

$$\frac{(\mu 30 \text{ s} - \mu 0)}{(\mu 0)(30 \text{ s})} = RH_{30 \text{ s}}$$

$\mu 30$ s—viscosity measured 30 seconds after Late Addition Premix 1 and 2 were added (Pa·s)

$\mu 10$ s—viscosity measured 10 seconds after Late Addition Premix 1 and 2 were added added (Pa·s)

$\mu 0$—viscosity measured of system prior to addition of rheology modifier (Pa·s)

TABLE 3

| Samples | 10 s Rate of Hydration (1/s) | 30 s Rate of Hydration (1/s) |
|---|---|---|
| High Water Sample | (0.45 Pa · s − 0.11 Pa · s) / ((0.11 Pa · s) (10 s)) = 0.309 | (1.98 Pa · s − 0.11 Pa · s) / ((0.11 Pa · s) (30 s)) = 0.567 |
| High Sorbitol Sample | (0.63 Pa · s − 0.59 Pa · s) / ((0.59 Pa · s) (10 s)) = 0.007 | (0.81 Pa · s − 0.59 Pa · s) / ((0.59 Pa · s) (30 s)) = 0.012 |
| Low Water Sample | (3.52 Pa · s − 3.52 Pa · s) / ((3.52 Pa · s) (10 s)) = 0.000 | (3.58 Pa · s − 3.52 Pa · s) / ((3.52 Pa · s) (30 s)) = 0.001 |

TABLE 3 shows the rate of hydration data for the Samples generated with the above method. The data supports that personal care compositions with wide ranges of rate of hydration can be produced with this late rheology methodology, in such a way that the majority of the rheology is built after leaving the process equipment. By having a relatively short average residence time in the process (around 60 seconds) and rates of hydration in the ranges described above, the process efficiencies, such as reduced down time between differing batches can be achieved.

In general, the rate of hydration data can be separated into high water, high sorbitol, and low water formulas. The test can clearly show how each solvent and rheology modifier system interact on short time scales resulting in viscosity changes. This rate of hydration (viscosity build) significantly impacts the efficiency and power requirements of the process system. For a fast hydrating system you need to minimize the time within the process system to improve efficiency. In theory if a system hydrates too slowly the product would not reach a consumer acceptable viscosity by the point of use.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of producing a personal care composition comprising:
   a) forming in a mix tank, an aqueous premix containing at least 10% water and having a lower viscosity than a packaged personal care composition;
   b) transferring the aqueous premix from the mix tank to a high energy dispersion device;
   c) adding rheology modifier in line to the aqueous premix as the aqueous premix is transferred through the high energy dispersion device;
   d) deaerating the aqueous premix; and
   e) packaging the aqueous premix to produce the packaged personal care composition.

2. The method of claim 1, wherein the transferring through the high energy dispersion device is at a flow rate of from about 10 Kg/min to about 1000Kg/min.

3. The method of claim 2, wherein deaerating is done through an inline deaeration device.

4. The method of claim 3, wherein, following addition of the rheology modifier to the aqueous premix, viscosity of the aqueous premix between the high energy dispersion device and inline deaeration device is between about 0.01 Pa·s and about 1,000 Pa·s measured at 10 sec−1.

5. The method of claim 3, wherein the inline deaeration device reduces the air level of the aqueous premix to about 0.01% or less, by volume of the aqueous premix.

6. The method of claim 1, wherein the rheology modifier is added in an amount from about 0.1% to about 10% by weight of the personal care composition.

7. The method of claim 1, wherein the rheology modifier is at least one of xanthan gum, carboxymethyl cellulose, carrageenan, carbomer, hydroxyethyl cellulose, guar gum, or thickening silica.

8. The method of claim 1, wherein the viscosity of the aqueous premix as it is transferred out of the mix tank is below about 150 Pa·s.

9. The method of claim 1 wherein, following addition of the rheology modifier to the aqueous premix, a surfactant is added to the aqueous premix following deaeration.

10. A method of producing a personal care composition comprising:
   a) forming in a mix tank, an aqueous premix containing at least 10% water and having a lower viscosity than a packaged personal care composition;
   b) transferring the aqueous premix from the mix tank to a high energy dispersion device;
   c) adding rheology modifier in line to the aqueous premix as the aqueous premix is transferred through the high energy dispersion device;
   d) deaerating the aqueous premix using an inline deaeration device; and
   e) packaging the aqueous premix to produce the packaged personal care composition; wherein the inline deaeration device is positioned such that pressure drop between the high energy dispersion device and inline deaeration device is less than pumping pressure head of the high energy dispersion device.

11. The method of claim 10, wherein, following addition of the rheology modifier to the aqueous premix, the viscosity of the aqueous premix between the high energy dispersion device and inline deaeration device is between about 0.01 Pa·s and about 1,000 Pa·s measured at 10 sec−1.

12. The method of claim 10, wherein the inline deaeration device reduces the air content of the aqueous premix to about 0.01% or less, by volume of the aqueous premix.

13. The method of claim 10, wherein the transferring through the high energy dispersion device is at a flow rate of from about 10Kg/min to about 1000Kg/min.

14. The method of claim 10, wherein the rheology modifier is added in an amount from about 0.1% to about 5% by weight of the personal care composition.

15. The method of claim 10, wherein the rheology modifier is at least one of xanthan gum, carboxymethyl cellulose, carrageenan, carbomer, hydroxyethyl cellulose, guar gum, or thickening silica.

16. The method of claim 10, wherein the viscosity of the aqueous premix as it is transferred out of the mix tank is below about 150 Pa·s.

17. The method of claim 10 wherein, following addition of the rheology modifier to the aqueous premix, a surfactant is added to the aqueous premix following deaeration.

18. The method of claim 17, wherein surfactant levels are from about 0.1% to about 15%, by weight of the personal care composition.

19. The method of claim 17, wherein the surfactant is at least one of anionic, amphoteric, non-ionic, zwitterionic or cationic surfactants.

* * * * *